(12) United States Patent
Lam

(10) Patent No.: US 9,980,849 B2
(45) Date of Patent: May 29, 2018

(54) OSTOMY APPLIANCE WAFER HAVING AN ABSORBENT LAYER LOCATED BETWEEN A FIRST ADHESIVE AND A SECOND ADHESIVE

(71) Applicant: Coloplast A/S, Humlebaek (DK)

(72) Inventor: Peter Kwok Hing Lam, Frederiksberg C (DK)

(73) Assignee: Coloplast A/S, Humlebaek (DK)

( * ) Notice: Subject to any disclaimer, the term of this patent is extended or adjusted under 35 U.S.C. 154(b) by 30 days.

(21) Appl. No.: 15/042,154

(22) Filed: Feb. 12, 2016

(65) Prior Publication Data

US 2016/0158057 A1    Jun. 9, 2016

Related U.S. Application Data

(63) Continuation of application No. 13/995,955, filed as application No. PCT/DK2011/050503 on Dec. 20, 2011, now Pat. No. 9,289,322.

(30) Foreign Application Priority Data

Dec. 22, 2010 (DK) .................................. 2010 70575

(51) Int. Cl.
*A61F 5/443* (2006.01)
*A61L 24/00* (2006.01)
*A61L 24/04* (2006.01)
*A61L 24/06* (2006.01)

(52) U.S. Cl.
CPC ............ *A61F 5/443* (2013.01); *A61L 24/001* (2013.01); *A61L 24/046* (2013.01); *A61L 24/06* (2013.01)

(58) Field of Classification Search
CPC combination set(s) only.
See application file for complete search history.

(56) References Cited

U.S. PATENT DOCUMENTS 5,175,246 A * 12/1992 Smith ............... A61K 9/7061
523/111
5,622,711 A * 4/1997 Chen ................ A61L 15/585
424/445

(Continued)

FOREIGN PATENT DOCUMENTS

GB    2041753 A1    9/1980
RU    2220685 C1    1/2004

*Primary Examiner* — Todd J Scherbel
*Assistant Examiner* — Guy K Townsend
(74) *Attorney, Agent, or Firm* — Coloplast Corp., Coloplast A/S; Nick Baumann

(57) ABSTRACT

An ostomy appliance wafer is provided with a stoma-receiving hole formed through the wafer. The wafer includes a backing layer, and an absorbent layer located between a first adhesive and a second adhesive. The first adhesive is disposed over the backing layer to define a peripheral edge area, a central area surrounding the hole, and an intermediate area of the wafer that is located between the peripheral edge area and the central area. The absorbent layer is disposed on the first adhesive either in A) the central area of the wafer, B) the intermediate area of the wafer, or C) the central area and the intermediate area of the wafer. The second adhesive is disposed over both a portion of an outer edge area of the absorbent layer and a portion of the first adhesive peripheral to the outer edge area of the absorbent layer.

15 Claims, 1 Drawing Sheet

(56) References Cited

U.S. PATENT DOCUMENTS

| | | | | |
|---|---|---|---|---|
| 5,714,225 | A * | 2/1998 | Hansen | A61F 5/443 424/443 |
| 5,951,533 | A * | 9/1999 | Freeman | A61F 5/443 604/338 |
| 8,207,393 | B2 * | 6/2012 | Bach | A61L 15/425 602/41 |
| 2005/0032952 | A1 * | 2/2005 | Bonfanti | C09J 131/04 524/306 |
| 2007/0060855 | A1 * | 3/2007 | Leung | A61L 15/225 602/41 |
| 2007/0179461 | A1 * | 8/2007 | Sambasivam | A61L 15/58 604/336 |
| 2007/0185464 | A1 * | 8/2007 | Fattman | A61F 5/443 604/336 |
| 2009/0030361 | A1 * | 1/2009 | Bach | A61L 15/425 602/54 |
| 2010/0204632 | A1 * | 8/2010 | Lykke | A61L 15/58 602/54 |
| 2011/0087182 | A1 * | 4/2011 | Stroebech | A61F 5/443 604/336 |
| 2013/0274696 | A1 * | 10/2013 | Lam | A61F 5/443 604/332 |

* cited by examiner

OSTOMY APPLIANCE WAFER HAVING AN ABSORBENT LAYER LOCATED BETWEEN A FIRST ADHESIVE AND A SECOND ADHESIVE

BACKGROUND OF THE INVENTION

1. Field of the Invention

The invention relates to an ostomy appliance for attachment to the body and for collecting bodily waste.

Ostomy appliances are usually in the form of a bag for receiving the waste, the bag being connected to an adhesive wafer that can be attached to the skin of the patient. The wafer is typically in the form of a backing layer coated on the skin-facing surface with an adhesive layer and the wafer is provided with an aperture for accommodating the body opening. The size and shape of said aperture can often be adapted individually to fit the anatomy of the patient.

One of the crucial parts of such devices is the adhesive wafer. The wafer should be able to fit leak proof around the body opening, have good adherence to the skin without unintended detachment from the skin, but at the same time be easy to remove again without damaging the skin. Furthermore, the wafer should be able to follow the movements of the body and be comfortable to wear.

Pressure sensitive adhesives have for a long time been used for attaching medical devices, such as ostomy appliances, dressings (including wound dressings), wound drainage bandages, fistula drainage devices, devices for collecting urine, orthoses and prostheses to the skin. Hydrocolloid adhesives, in particular, are used for ostomy appliances.

The hydrocolloid adhesives contain hydrophilic particles or absorbents, which absorb moisture into the adhesive bulk and transmit moisture when conditions are saturated. However, the retention of moisture in hydrocolloid adhesives may cause changes in the adhesive, such as swelling, loss of cohesion and disintegration.

Due to the delicate nature of skin, there is a narrow window where a pressure sensitive adhesive can function as a good, skin friendly adhesive: On one hand, the adhesive should be able to provide a strong and secure attachment of the medical device to the skin, thus avoiding leakage and unintentional detachment of the device, but on the other hand, removal of the medical device from the skin should be painless and not cause damage to the skin.

Conventional pressure sensitive adhesives for collecting devices are usually based on adhesives that flow into the skin. This makes the adhesive very sticky to the skin, but also means that when the adhesive is removed; part of the top layer of the skin or epidermis is peeled off, a phenomenon known as skin stripping.

2. Description of the Related Art

WO 94/15562 and U.S. Pat. No. 5,051,259 disclose adhesive wafers wherein the skin-facing surface comprises at least two different adhesives. The adhesives are preferably hydrocolloid adhesives of different cohesion.

Thus, there is still a need for an ostomy appliance with reduced skin stripping but yet capable of secure attachment to the skin.

SUMMARY OF THE INVENTION

The present invention aims at providing an ostomy appliance, which improves the comfort for the patient by reducing skin stripping and eliminates or at least to a large extent reduces the risk of leakage and unintentional detachment of the appliance.

An object of the invention is to provide an ostomy appliance with a skin-friendly adhesive, being easy and less painful to remove from the skin.

Another object of the present invention is to provide an ostomy appliance which is less sensitive when exposed to moisture.

BRIEF DESCRIPTION OF THE DRAWINGS

The invention is disclosed more in detail with reference to the drawings wherein.

DETAILED DESCRIPTION OF THE PRESENT INVENTION

Figure 1:
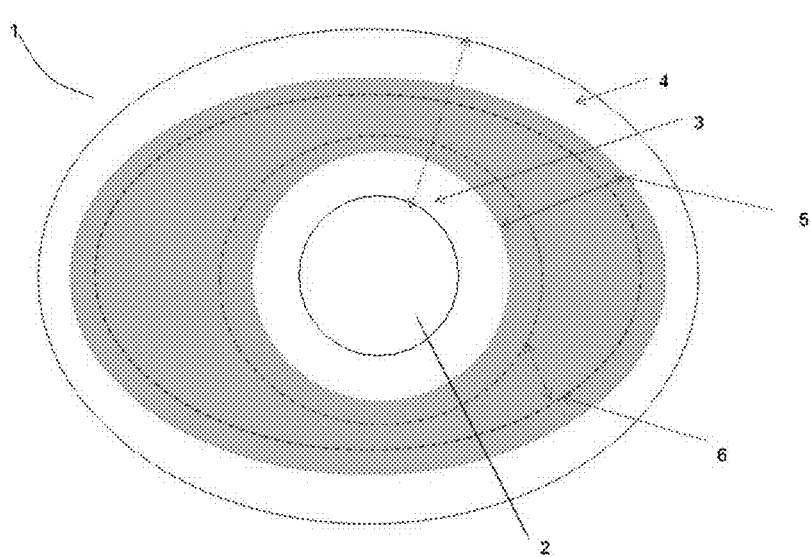
FIG. 1 shows a preferred embodiment of the invention seen from the skin facing side.

The invention relates to an ostomy appliance comprising an adhesive wafer for attachment to the body, the wafer comprises a central aperture for accommodating a stoma and a skin facing surface and a non skin-facing surface, the non skin-facing surface being provided with a backing layer, the skin facing surface of the wafer comprises a central area comprising a substantially non-absorbent protective adhesive, an intermediate area surrounding the central area, said area comprising a substantially non-absorbent soft adhesive, and an edge area surrounding the intermediate area, said edge area comprising a substantially non-absorbent protective.

The combination of a strong protective adhesive at the border portions and a soft, skin-friendly adhesive on the middle portion of the wafer unites the advantages of both adhesives by providing a good tack and leakage control along the borders together with a minimum of skin stripping at the rest of the adhesive surface of the wafer.

The central area and the edge area may be in the form of separate areas or the protective adhesive may overlie the non-skin facing surface of the soft adhesive. The protective adhesive may thus cover the entire skin-facing surface of the backing layer and the soft adhesive constitutes a layer overlying a part of the skin-facing surface of the protective adhesive.

The use of the soft adhesive on its own, will often not be sufficient to provide the degree of protection required against aggressive outputs e.g. from stomas. The combined use of protective and soft adhesive will reduce the cell stripping effect compared to the use of strong adhesive alone, but at the same time being able to maintain the advantages of the strong adhesive by providing protection against output and securing effective attachment to the skin.

The device of the present invention is soft and comfortable to wear, having a good adhesive tack, but is yet easy and gentle to remove and is permeable to moisture, thus overcoming the drawbacks of the hydrocolloid adhesive devices. The soft adhesive is resistant to erosion and does not lose its tack when exposed to moisture.

The device may be removed with minimal pain due to extreme flexibility and less skin cells stripped off and thus less traumatisation of skin. The soft adhesive has a broad peel front and good tenacity during use. The soft adhesive is resistant to erosion and has a good moisture handling capacity due to high moisture vapor permeability.

By using a substantially non-absorbent adhesive, traditional problems occurring when exposed to moisture such as erosion, weakening of properties in use due to swelling and disintegration are diminished. The intermediate area facilitates reduced stripping and provides gentleness to the skin. The protective adhesive on the outer edge allows the user to have time to react if leakage has penetrated through the central area and the intermediate area.

The construction of the appliance according to the invention facilitates delayed leakage over the wafer, leaving time for the user to change the wafer before the leakage reaches the outside of the wafer.

Having a layer of non-absorbent adhesive facing the skin combined with an absorbent layer facing the backing layer provides a skin-friendly attachment to the skin being capable of transporting moisture away from the skin and into the absorbent layer.

The protective adhesive may be any skin adhesive known per se, e.g. an acrylic adhesive or a hydrogel adhesive. The adhesive material may e.g. comprise synthetic homo-, co- or block-copolymers, polyacrylate and copolymerisates thereof, polyurethane, silicone, polyisobutylene, polyvinyl ether and natural or synthetic resins or mixtures thereof optionally containing zinc oxide. The adhesive matrix may further contain various additives, such as plasticizers, thickeners and others, and/or various medicaments, such as antiseptics, hormones, etc.

Particularly preferred would be pressure sensitive adhesives with high peel force. By high peel force is meant a peel force above 2 N/25 mm on steel, more preferred from 3 to 20 N/25 mm. Peel force is measured by the approved standard ASTM D6862-04.

The soft adhesive of the intermediate area is a soft, non-skin-stripping adhesive.

Such soft adhesive may comprise a cross-linked adhesive, such as silicone, acrylic or polyurethane adhesives. As used herein a cross-link means a small region in a macromolecule (polymer chain structure) from which more than 2 chains emanate.

In a preferred embodiment, the soft adhesive is silicone based, such as an adhesive comprised of a chemically cross-linked silicone gel (polydimethyl siloxane gel), for instance a platinum catalyzed 2-component addition hardening RTV-silicone. Examples of gels that can be used are SilGel 612 from Wacker-Chemie GmbH, Burghausen, Germany, MED-6340 from NuSil Technology, DOW CORNING® MG 7-9900 SOFT SKIN ADHESIVE.

The soft adhesive may comprise a polyalkyleneoxide polymer and organosiloxane based cross-linked adhesive system. The polyalkylene oxide polymer may be polypropyleneoxide.

The soft adhesive may comprise ethylene vinyl acetate. Examples of such adhesive are disclosed in WO 2009/006901.

By soft adhesive layer is meant an adhesive with a complex modulus G* as defined herein of less than 100 kPa measured at 32° C. and 1 Hz.

In a preferred embodiment, the soft adhesive has a complex modulus G* of less than 1-30 kPa measured at 32° C. and 1 Hz.

Particularly preferred would be hydrophobic pressure sensitive adhesives with low peel force. By low peel force is meant a peel force above 0.5 N/25 mm on steel, more preferred a peel force of 1 to 10 N/25 mm.

The nature of the soft adhesive used in this invention differs from the nature of adhesives that are typically used, for instance hydrocolloid adhesives that are used today for ostomy wafers. The significant difference between these adhesives and the soft adhesive used in accordance with the invention is that the soft adhesive is much softer and has a better "wetting ability" meaning more surface contact. This enables the soft adhesive to be given a much lower specific adhesiveness, i.e. lower adhesion per unit of contact surface area.

This is the reason why the patient will feel very little pain when the soft adhesive is removed and removal can be achieved without stripping cells from the surface layer of the skin, in contradistinction to the effect of typically used more aggressive adhesives. The adhesive force between the soft adhesive and skin is optimized in accordance with the following principle: adhesion shall be as strong as possible without risk of the surface layer of the epidermis being removed by the adhesive layer when the adhesive is removed.

The adhesive compositions of the appliance according to the invention may contain other conventional ingredients for adhesive compositions, such as tackifiers, extenders, non-reactive polymers, oils (e.g. polypropylenoxide, ethyleneoxide-propyleneoxide copolymers, mineral oil), plastizisers, fillers, and surfactants. The adhesive may also comprise pharmaceutically active ingredients. These optional ingredients may be present in the reaction mixture during the cross linking reaction.

The backing layer of the adhesive wafer may e.g. be a water impervious layer or film, may be of any suitable material known per se for use in the preparation of ostomy adhesive wafers or wound dressings e.g. a foam, a non-woven layer or a polyurethane, polyethylene, polyester or polyamide film.

The water impervious layer or film is preferably a low-friction flexible polymer film reducing the risk of unwanted stress in an exposed area. A suitable material for use as water impervious layer is a film conventionally used as backing layer in the preparation of wound dressings, suitably having a thickness of about 30 microns.

An especially suitable material for use as a water impervious film is a polyurethane film. A preferred low friction film material is disclosed in U.S. Pat. No. 5,643,187.

Preferably, the backing layer has thermoplastic elements that enable welding of e.g. a pouch or coupling ring to the adhesive wafer. Preferred thickness of the backing layer is between 10-60 µm in order to maintain the softness of the adhesive wafer.

The absorbent layer may be any suitable absorbent material or mixtures thereof, such as CMC (carboxy methylcellulose), SAP/SAF (super absorbent particles or fibers), salt, sandwich layers including nonwovens, within permeable polymer matrix.

The absorbent layer may be 10 to 2000 µm in thickness.

Absorbent layer should be min. 5 mm from both borders of gentle adhesive. The absorbent layer may be sandwiched between the protective and the soft adhesive and the edge portions of the soft adhesive may preferably overlap the edge portions of the absorbent layer. The edge portions of the absorbent layer are thus not exposed on the skin-facing surface of the wafer.

In order to enhance the permeability of the soft adhesive, the intermediate layer may be provided with a plurality of perforations such as holes. The holes of the soft adhesive will also facilitate fast absorption into the absorbent layer if such is present, and thereby reducing the exposure to moisture to the soft adhesive. In this way, moisture will not affect the performance of the soft adhesive as the adhesive itself does not have any absorption.

The perforations may be in the form of a pattern of holes or the soft adhesive may have a net-like configuration, for example pattern coated.

The protective adhesive may be provided with a plurality of holes. Such holes may be in the central portion or they may be in the entire protective adhesive. An absorbent layer may be provided between the backing layer and the protective adhesive with holes.

With a construction where the protective adhesive extends over the non-skin facing surface of the soft adhesive, production may be simple as the soft adhesive is placed on top of the protective adhesive without need for further lamination. The wafer of the invention may e.g. be manufactured by molding or by lamination.

The wafer may have any suitable configuration for ostomy adhesive plates, but is preferably substantially circular or oval/elliptic.

The intermediate area may constitute at least 50% of the skin-facing surface.

In order to ensure good adhesion to the skin and avoid leakage, it is preferred that the central area comprising the protecting adhesive has a minimum width of 15 mm, after cutting off a central aperture for accommodating the stoma (the width measured from the edge of the aperture).

Preferably, the edge area has a width of at least 5 mm.

The intermediate area may preferably constitute at least 50% of total adhesive area.

The thickness of the protective adhesive may be 50 to 1000 μm at exposed areas such as the central and the edge areas, and 10 to 200 in construction zone, the part overlying the intermediate area.

The soft adhesive layer may have a thickness of 10-20000 μm, more preferred 10-300 μm.

Yet another advantage of the device according to the described embodiment is that it maintains its integrity upon contact with fluid. In this context it should be noted that if the opening of the device is too small, it could be made larger by punching or cutting in order to adapt its size to the stoma. Conventional fastening arrangements for stoma bags are often provided with cutting marks, for example in the form of helical lines, to make this kind of adaptation easier. Such adaptation of size is important for ensuring that the smallest possible area of skin around the stoma comes into contact with the intestinal content collected in the stoma bag. The shapeability of the device means that it is easy to finely adjust the shape of the opening in a way that this coincides with the cross-sectional shape of the stoma, which may deviate from a circular shape.

By substantially non-absorbent is herein meant an absorption of less than 10%, preferably less than 5% by wt in 24 hrs.

The collecting pouch may be detachable from the adhesive wafer by a coupling system or the pouch and the wafer may be integrated with the wafer, e.g. by welding. The two versions are known as one piece or two-piece appliances for ostomy.

In order to avoid rolling up of the edge portion during wear, it may be advantageous to bevel the edge portion of the wafer.

A protective cover or release liner may for instance be siliconized paper. The protective cover is not present during the use of the adhesive plate of the invention and is therefore not an essential part of the invention.

DESCRIPTION OF THE PREFERRED EMBODIMENTS

The invention is now explained more in detail with reference to the drawings showing preferred embodiments of the invention.

In FIG. 1 is shown a preferred embodiment of the invention seen from the skin-facing side of the wafer. An adhesive wafer 1 comprises a central aperture 2 for accommodating a stoma, a central area 3 and an edge area 4 and an intermediate area 5 there between. The edge area 4 and the central area 3 comprise a protective adhesive whereas the intermediate area 5 comprises a soft adhesive. An absorbent layer 6 is placed on the non-skin-facing surface of the soft adhesive 5 but has a smaller width than the soft adhesive 5 facilitating that the absorbent layer 6 is not directly exposed to the skin-facing surface. The entire absorbent layer 6 is covered by the soft adhesive 5 and the soft adhesive 5 overlaps the edges of the absorbent layer 6.

Figure 2:
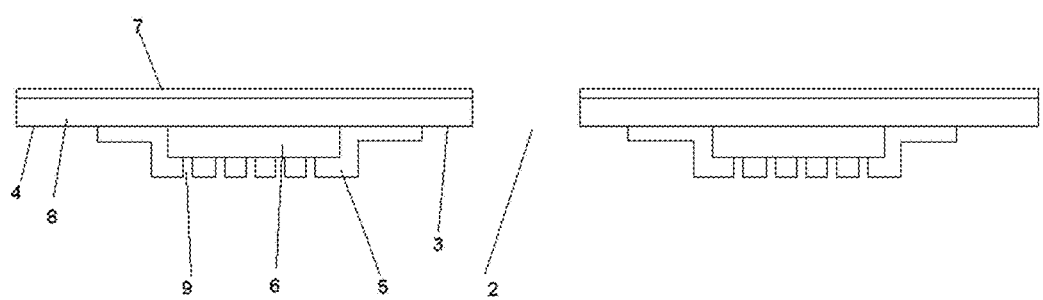
FIG. 2 shows an embodiment of the invention in cross-section.

FIG. 2 shows the wafer 1 of the invention in cross-section. The wafer comprises a backing layer 7 covered on the skin facing surface with a protective adhesive 8. An intermediate area 5 is encircling the central area 2 and the central aperture 2 and comprises a soft adhesive and optionally an absorbent layer 6. The location of the soft adhesive 5 provides a skin-facing surface of the wafer 1 that is constituted by a central portion 3 with protective adhesive and intermediate portion 5 with soft adhesive and an edge 4 portion with protective adhesive. The absorbent layer 6 is sandwiched between the protective 8 and the soft adhesive 5 and the edge portions of the soft adhesive 5 overlaps the edge portions of the absorbent layer 6 and the absorbent layer 6 is thus not exposed on the skin-facing surface of the wafer 1. The protective adhesive 8 extends over the non-skin facing surface of the soft adhesive 5 and the absorbent layer 6. The soft adhesive 5 may be provided with a plurality of holes 9.

Materials and Methods

Determination of G*

The parameter G* or complex modulus as defined in "Dynamics of polymeric liquids", Vol. 1, sec. ed. 1987, Bird, Armstrong and Hassager, John Wiley and Sons inc., was used as a measure of the hardness of an adhesive. G* at 32° C. and 0.01 Hz was measured as follows: A plate of un-foamed adhesive material was pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurement was carried out at 32° C.

What is claimed is:

1. An ostomy appliance wafer having a hole formed through the wafer sizable to receive a stoma, the ostomy appliance wafer comprising:
   a backing layer; and
   an absorbent layer located between a first adhesive and a second adhesive;
   wherein the first adhesive is disposed over substantially all of the backing layer to define a peripheral edge area, a central area surrounding the hole, and an intermediate area of the wafer that is located between the peripheral edge area and the central area, with the absorbent layer disposed on the first adhesive in one of A) the central area of the wafer, B) the intermediate area of the wafer, or C) the central area and the intermediate area of the wafer;
   wherein the absorbent layer has a non-skin facing side in contact with the first adhesive, a skin-facing side opposite of the non-skin facing, side, and an outer edge area connecting the non-skin facing side and the skin-facing side;
   wherein the second adhesive is disposed over the outer edge area and the skin-facing side of the absorbent layer and a portion of the first adhesive peripheral to the outer edge area of the absorbent layer; and wherein the second adhesive is substantially non-absorbent to stoma output.

2. The ostomy appliance wafer of claim 1, wherein the second adhesive is disposed over the outer edge area of the absorbent layer, the portion of the first adhesive peripheral to the outer edge area of the absorbent layer, and a portion of the first adhesive that is inside of an inner edge area of the absorbent layer.

3. The ostomy appliance wafer of claim 1, wherein the first adhesive is a substantially non-absorbent adhesive.

4. The ostomy appliance wafer of claim 1, wherein the first adhesive has a peel force in a range of 2-20 N/25 mm on a steel and the second adhesive has a complex modulus in a range from 1-100 kPa measured at 32 degrees Celsius and 1 Hz.

5. The ostomy appliance wafer of claim 1, wherein a peel strength of the second adhesive is less than the peel force of the first adhesive.

6. The ostomy appliance wafer of claim 1, wherein the first adhesive and the second adhesive are not hydrocolloid adhesives.

7. The ostomy appliance wafer of claim 1, wherein the second adhesive comprises a cross-linked adhesive.

8. The ostomy appliance wafer of claim 1, wherein the second adhesive comprises a silicone adhesive.

9. The ostomy appliance wafer of claim 1, wherein the first adhesive is selected from the group consisting of synthetic homopolymers, copolymers, block-copolymers, polyacrylate and copolymerisates of polyacrylate, polyurethane, silicone, polyisobutylene, polyvinyl ether, natural resin, synthetic resin, and mixtures of natural and synthetic resin.

10. The ostomy appliance wafer of claim 1, wherein the second adhesive has a peel force in a range from 1 N/25 mm to 10 N/25 mm on steel.

11. The ostomy appliance wafer of claim 1, wherein the second adhesive is provided with a plurality of holes.

12. The ostomy appliance wafer of claim 1, wherein the intermediate area of the wafer is at least 50% of a total area of the wafer.

13. The ostomy appliance wafer of claim 1, further comprising:

a detachable collecting pouch that is attachable to the backing layer of the wafer.

14. The ostomy appliance wafer of claim 1, further comprising:

a collecting pouch integrated with the backing layer of the wafer.

15. An ostomy appliance wafer having a hole formed through the wafer sizable to receive a stoma, the ostomy appliance wafer comprising:

a backing layer; and an absorbent layer sandwiched between a first adhesive and a second adhesive, where the first adhesive and the second adhesive are substantially non-absorbent to stoma output;

wherein the first adhesive is disposed over substantially all of the backing layer to define a peripheral edge area, a central area surrounding the hole, and an intermediate area of the wafer that is located between the peripheral edge area and the central area, with the absorbent layer disposed on the first adhesive in one of A) the central area of the wafer, B) the intermediate area of the wafer, or C) the central area and the intermediate area of the wafer; and wherein the second adhesive is disposed over a portion of an outer edge area of the absorbent layer, a portion of the first adhesive peripheral to the outer edge area of the absorbent layer, and a portion of the first adhesive that is inside of an inner edge area of the absorbent layer such that the absorbent layer is not exposed to skin of a person wearing the ostomy appliance.

* * * * *